(12) United States Patent
Sakakibara et al.

(10) Patent No.: US 11,026,705 B2
(45) Date of Patent: Jun. 8, 2021

(54) FILTER DEVICE

(71) Applicant: Toray Industries, Inc., Tokyo (JP)

(72) Inventors: Hajime Sakakibara, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 165 days.

(21) Appl. No.: 16/490,236

(22) PCT Filed: Mar. 13, 2018

(86) PCT No.: PCT/JP2018/009669
§ 371 (c)(1),
(2) Date: Aug. 30, 2019

(87) PCT Pub. No.: WO2018/168832
PCT Pub. Date: Sep. 20, 2018

(65) Prior Publication Data
US 2020/0000482 A1 Jan. 2, 2020

(30) Foreign Application Priority Data

Mar. 13, 2017 (JP) .............................. JP2017-047184

(51) Int. Cl.
*A61F 2/01* (2006.01)
*A61B 17/22* (2006.01)
(52) U.S. Cl.
CPC ................ *A61B 17/22* (2013.01); *A61F 2/01* (2013.01); *A61F 2/011* (2020.05);
(Continued)

(58) Field of Classification Search
CPC .. A61F 2/01; A61F 2/012; A61F 2/013; A61F 2/014; A61F 2/0105;
(Continued)

(56) References Cited

U.S. PATENT DOCUMENTS

2004/0243173 A1 12/2004 Inoue
2007/0112374 A1* 5/2007 Paul, Jr. .................. A61F 2/013
606/200
(Continued)

FOREIGN PATENT DOCUMENTS

JP 4067353 B2 3/2008
JP 5749094 B2 7/2015
(Continued)

*Primary Examiner* — Tuan V Nguyen
(74) *Attorney, Agent, or Firm* — DLA Piper LLP (US)

(57) ABSTRACT

A filter device is capable of reliably capturing emboli and air bubbles and reliably removing the captured emboli out of the body. The filter device includes: a first tube; a second tube protruding from the first tube; a filter arranged such that the distal end side of the filter in the longitudinal direction forms an opening; a ring fixed to the opening; first wires protruding from the distal end side of the first tube in the longitudinal direction thereof; and second wires protruding from holes in the first tube and fixed to the ring; wherein the opening can be opened and closed in the form of a bag when the proximal end side of the filter in the longitudinal direction is defined as the bottom, and the opening can be closed by pulling the second tube towards the proximal end side in the longitudinal direction.

4 Claims, 7 Drawing Sheets

(52) U.S. Cl.
CPC . *A61F 2002/016* (2013.01); *A61F 2230/0069* (2013.01); *A61F 2230/0093* (2013.01)

(58) Field of Classification Search
CPC ........ A61F 2002/016; A61F 2230/0069; A61F 2230/0093; A61B 17/22; A61B 2017/2215
See application file for complete search history.

(56) References Cited

U.S. PATENT DOCUMENTS

| | | | |
|---|---|---|---|
| 2009/0222035 A1* | 9/2009 | Schneiderman | A61B 17/221 606/200 |
| 2012/0239064 A1 | 9/2012 | Cartier et al. | |
| 2013/0253571 A1* | 9/2013 | Bates | A61F 2/013 606/200 |
| 2014/0236220 A1 | 8/2014 | Inoue | |
| 2014/0277015 A1 | 9/2014 | Stinis | |

FOREIGN PATENT DOCUMENTS

| | | |
|---|---|---|
| WO | 03/030740 A1 | 4/2003 |
| WO | 2013/047623 A1 | 4/2013 |

\* cited by examiner

FILTER DEVICE

TECHNICAL FIELD

This disclosure relates to a filter device that captures thrombi and the like.

BACKGROUND

Atrial fibrillation is one type of cardiac arrhythmia, and is known as a condition in which irregular arterial contractions occurs repeatedly to deteriorate blood circulation, thereby causing discomfort and a feeling of fatigue. Accordingly, methods of treating atrial fibrillation by catheter ablation procedures have been widely used in recent years in which procedures, myocardial tissues such as pulmonary veins and the posterior wall of the left atrium in the vicinity of the pulmonary veins, which are primary sites of occurrence of atrial fibrillation, are thermally ablated.

However, those procedures have a problem in that a thrombus having been formed due to deterioration of blood circulation, or a thrombus formed due to the heat of the ablation procedure at an affected site or on a medical device, may be carried away by the blood flow recovered by the treatment, possibly causing infarction in a peripheral blood vessel.

At present, there have been developed filter devices to receive substances such as released thrombi, plaques and the like to avoid the risk of occurrence of infarction in peripheral blood vessels and the like. As an example of such a filter device, a device that captures emboli has been reported which can be used when carrying out a surgery or a procedure that may possibly cause formation of emboli upstream of the blood flow (JP 5749094 B2). Further, there has also been reported an intravascular blood filter that can be placed in and removed from a blood vessel, in which the opening of the filter being in close contact with the inner wall of an artery in a favorable manner, and is capable of reliably capturing tissue pieces (JP 4067353 B2).

When capturing a thrombus having been formed due to deterioration of blood circulation or a thrombus generated from a thermally ablated portion during an ablation procedure, by a filter, before the thrombus is carried away by the blood flow recovered by the treatment and flows to a peripheral organ such as the brain, it is desired that the filter can be removed out of the body with the opening of the filter securely closed so that the captured embolus can be prevented from being released into the body again.

The device that captures emboli disclosed in JP 5749094 B2 is configured such that the opening of a filter portion is arranged to face the distal end side of a shaft member so that the blood flow and opening are opposed to each other, and the filter portion is folded and closed by being stowed inside a microcatheter. However, since the filter portion does not have a closure mechanism, there is a possibility that the captured emboli may be released when the filter portion fails to be properly folded upon stowing.

Further, the intravascular blood filter disclosed in JP 4067353 B2 includes: wires for pulling forward that connect a member that opens and closes the filter with a core material; and wires for pulling backward that connect a filter ring with a catheter member. In the intravascular blood filter, the opening of the filter portion is opened and closed by deformation and restoration of the member that opens and closes the filter, which are achieved by the movement of the core material relative to the catheter member, in the axial direction. However, in the intravascular blood filter, the core material functions as a guide wire, and when the function of the core material as a guide wire that guides the filter to a target site is used during the procedure, the core material as the guide wire is rotated, and there is a possibility that the wires for pulling may be entangled with the core material or the catheter member. Thus, the opening of the filter portion may not be sufficiently controlled, possibly resulting in a failure to capture the emboli generated during the procedure.

Therefore, it could be helpful to provide a filter device in which the opening and closing of the opening of the filter portion can be sufficiently controlled to capture emboli and remove the captured emboli out of the body without releasing them from the filter portion.

SUMMARY

We thus provide:
(1) A filter device including:
a first tube having holes on the side surface thereof;
a second tube inserted through the first tube and protruding from the proximal end side of the first tube in the longitudinal direction thereof;
a filter arranged such that the filter has a closed end portion on the proximal end side in the longitudinal direction of the first tube, and such that the distal end side of the filter in the longitudinal direction forms an opening;
a ring fixed to the opening and having elasticity or shape memory property;
first wires inserted between the first tube and the second tube, wherein the proximal ends of the first wires are fixed to the second tube, and the distal ends of the first wires protrude from the distal end side of the first tube in the longitudinal direction thereof and are fixed to portions of the ring; and
second wires inserted between the first tube and the second tube, wherein the proximal ends of the second wires are fixed to the second tube, and the distal ends of the second wires protrude from the holes and are fixed to portions of the ring;
wherein the opening can be opened and closed in the form of a bag when the proximal end side of the filter in the longitudinal direction is defined as the bottom, and the opening can be closed by pulling the second tube towards the proximal end side in the longitudinal direction.
(2) The filter device according to (1), wherein the holes are arranged to form equal angles relative to the central axis of the first tube, and arranged on the same circumference.
(3) The filter device according to (1) or (2),
wherein the ring has a cylindrical shape, and
wherein the fixed positions of the first wires to the ring, and the fixed positions of the second wires to the ring, are arranged alternately relative to the central axis of the first tube.
(4) The filter device according to (1) or (2),
wherein the ring includes a plurality of mountains facing the distal end side in the longitudinal direction, and a plurality of valleys facing the proximal end side in the longitudinal direction, which mountains and valleys are alternately formed,
wherein the fixed positions of the first wires to the ring are provided at the apices of the mountains, and
wherein the fixed positions of the second wires to the ring are provided at the bottoms of the valleys.

It is thus possible to reliably and easily close the opening of the filter since an operation of moving the second tube relative to the first tube allows the first wires and the second wires to open and close the opening of the filter. As a result, it becomes possible to remove the captured emboli out of the body without allowing them to flow out of the filter portion.

Further, a guide wire can be inserted through the lumen of the second tube, and the filter device can be delivered along the guide wire placed in a blood vessel in advance, and thus there is no need to rotate the device.

The ring fixed to the opening is made of a wire having elasticity or shape memory property so that the ring can be expanded in the direction vertical to the longitudinal direction. Therefore, the filter opening can be self-expanded outward in the direction vertical to the longitudinal direction, thereby allowing for an improved adhesion to the inner wall of a blood vessel, and enabling to reliably capture emboli such as thrombi and air bubbles formed due to an endovascular treatment or the like.

The ring has a cylindrical shape, and the fixed positions of the first wires to the ring, and the fixed positions of the second wires to the ring, are arranged alternately relative to the central axis of the first tube. Therefore, the filter can be deformed in a favorable manner to ensure a more reliable closure of the opening.

Further, when the wires are pulled to the proximal end side, the ring is deformed in the form of waves, due to the difference in pulling capacity between the first wires and the second wires, and thus, the closure of the opening can further be improved.

According to the above described invention, the ring has a shape that includes a plurality of mountains facing the distal end side in the longitudinal direction, and a plurality of valleys facing the proximal end side in the longitudinal direction, which mountains and valleys are alternately formed. Further, the fixed positions of the first wires to the ring are provided at the apices of the mountains, and the fixed positions of the second wires to the ring are provided at the bottoms of the valleys. Therefore, the filter can be deformed in a favorable manner to ensure a more reliable closure of the opening.

DESCRIPTION OF SYMBOLS

Figure 1:
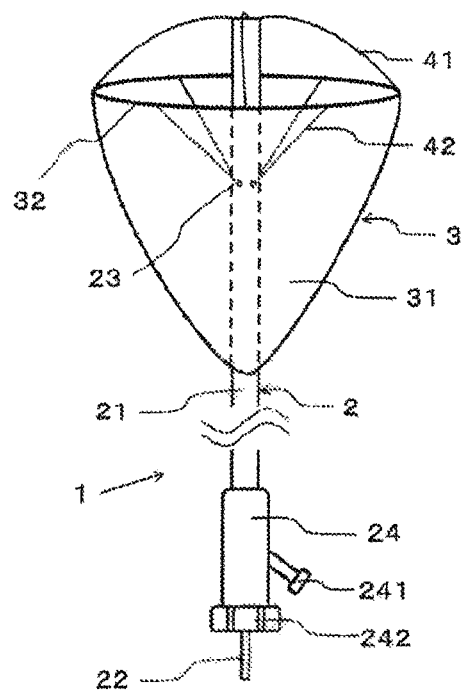
FIG. 1 is an explanatory diagram showing a first example of the filter device.

1: Filter device
2: Body portion
3: Filter portion
10, 13: Filter device,
5: Intravascular blood filter
21: First tube
22: Second tube
23: Hole
24: Connector
31: Filter member
32, 33: Ring
41: First wire
42: Second wire
51: Sore material
52: Catheter member
53: Filter member
54: Filter ring
55: Wire for pulling forward
56: Wire for pulling backward
100: Tube
110: Sheath introducer
120: Simulated embolic particles
241: Liquid inflow port
242: Hemostasis valve

DETAILED DESCRIPTION

Specific examples will now be described with reference to the drawings. However, this disclosure is in no way limited to these examples. The proportions of the drawings do not necessarily match those of the description.

FIRST EXAMPLE

FIG. 1 is a schematic diagram of a filter device 1 according to the first example. The filter device 1 is used, for example, when carrying out a catheter ablation procedure for treating atrial fibrillation, as a device for preventing a situation where a thrombus that has been formed due to deterioration of blood circulation or a thrombus generated from a thermally ablated portion is carried away by the blood flow recovered by the treatment, and flows into a peripheral blood vessel, to cause the occurrence of an infarction. The filter device 1 according to the first example includes: a body portion 2 that allows the filter portion to be moved to a target site within a blood vessel; a filter portion 3 that captures thrombi; and first wires 41 and second wires 42 that open and close the opening of the filter portion 3.

The body portion 2 includes: a first tube 21; and a second tube 22 inserted through the lumen of the first tube 21. The second tube 22 is configured such that the proximal end of the second tube 22 protrudes from the proximal end side of the first tube 21, and such that the second tube 22 can be moved relative to the first tube 21. Further, a guide wire can be inserted through the lumen of the second tube 22. By this arrangement, the body portion 2 can be moved along the guide wire placed in a blood vessel in advance, thereby enabling delivery of the filter device 1 to a target affected site.

The first tube 21 includes holes 23 through which the second wires 42 to be described later can be inserted. The first tube 21 preferably includes a plurality of the holes 23 in a number corresponding to the number of the second wires 42. Further, when the first tube 21 includes a plurality of the holes 23, the holes 23 are arranged to form substantially equal angles relative to the central axis of the first tube 21, and arranged in the same circumferential direction. The first tube 21 in the first example includes as shown in FIGS. 2(a) and (b), four holes 23 arranged in the same circumferential direction, and the four holes 23 are arranged at such intervals that respective two adjacent holes 23 form 90 degrees relative to the central axis of the first tube 21. Further, a connector 24 is fixed to the proximal end side of the first tube 21 in the longitudinal direction.

As the materials of the first tube 21 and the second tube 22, any material having flexibility may be used. Examples thereof include: polyolefins such as polyurethane, polyamide, silicone, polypropylene and polyethylene; as well as thermoplastic resins such as polyether ketone resins (PEEK), fluorine resins, ethylene-tetrafluoroethylene copolymers (ETFE) and polytetrafluoroethylene resins (PTFE) and polyimide resins.

When a resin such as polyamide or polyimide is used as the material of the first tube 21, an easily slidable resin such as polytetrafluoroethylene may be incorporated into an inner layer to improve the slidability of the second tube 22. Further, it is also possible to incorporate a braided layer formed using a metal wire such as a stainless steel wire, or a resin such as polyamide to ensure rigidity of the tube.

The first tube 21 preferably has a length of about 700 to 1,250 mm, for example, when inserting the filter device 1 from the femoral artery to be placed in the ascending aorta. Further, the first tube 21 preferably has an outer diameter of about 1.5 to 3.3 mm, and more preferably about 1.7 to 3.3 mm.

As the first tube 21, a tube formed as an integrated tube may be used, or alternatively, a tube composed of a plurality of tubes may be used.

Further, the surface of the first tube 21 is preferably subjected to an antithrombogenic treatment since thrombi may be adhered to or formed on the surface of the tube.

The second tube 22 is required to have a length longer than that of the first tube 21, and preferably has a length of about 800 to 1,350 mm. Further, the second tube 22 is required to have an inner diameter through which a guide wire commonly used in a catheter treatment for the circulatory system can be inserted. The second tube 22 preferably has, for example, an inner diameter of about 0.40 to 1.00 mm so that a guide wire having a diameter of 0.014 to 0.035 inches can be inserted therethrough.

To facilitate insertion of a guide wire into the lumen of the second tube 22, it is preferred that the second tube 22 be configured such that the distal end thereof coincides with, or protrudes from, the distal end of the first tube 21, when the filter portion 3 is opened. By the above described configuration, it becomes possible to easily insert the guide wire into the lumen of the second tube 22.

The connector 24 is fixed to the proximal end side of the first tube 21 as shown in FIG. 1 and includes: a liquid inflow port 241 capable of injecting a physiological saline solution or the like into the lumen of the first tube 21; and a hemostasis valve 242 that prevents the leaking of blood when the second tube 22 is operated and not operated. It is more preferred that the hemostasis valve 242 be configured such that the valve can be opened and closed by a rotary motion or the like. By the above described configuration, the second tube 22 can be operated when the hemostasis valve 242 is opened, and the second tube 22 can be fixed when the hemostasis valve 242 is closed.

The filter portion 3 includes: a filter 31 in the form of a bag; and a ring 32 which has a cylindrical shape fixed to the opening of the filter 31, and contributes to the opening and closing of the opening. As shown in FIG. 1, the filter 31 in the first example is in the form of a bag, and configured such that the bottom of the bag located at the proximal end side in the longitudinal direction of the first tube, serves as the closed end portion, and the opening of the bag located at the distal end side in the longitudinal direction, serves as the opening.

The filter 31 is disposed at the distal end side in the longitudinal direction of the filter device 1. Further, in the filter device 1 according to the first example, the closed end portion of the filter 31 is fixed to the first tube 21, and the entire shape of the filter device 1 is the shape of an umbrella opened upside down. In placing the filter device 1 in the ascending aorta, for example, the opening of the filter portion 3 preferably has a diameter of about 25 to 40 mm.

As another example different from the first example, the filter device may include a third tube arranged to be movable on the first tube 21. The third tube is configured to have an inner diameter larger than that of the first tube, and a length shorter than that of the first tube so that the third tube can be moved relative to the first tube 21. When the filter device includes the third tube, the filter 31 may be fixed to the third tube. In this example, the length of the filter 31 in the longitudinal direction can be changed by moving the third tube on the first tube 21. Further, the third tube preferably has such an inner diameter that the gap between the first tube 21 and the third tube is 500 μm or less so that the captured emboli can be prevented from being released.

The filter 31 in the first example is prepared by forming a polymer in the form of a sheet, forming a plurality of pores in the sheet, and then forming the sheet in the form of a bag. However, to increase the aperture ratio of the filter, and ensure a sufficient passage rate of blood, the filter 31 may also be prepared by forming fibers of a polymer or a metal in the form of a mesh, and forming the mesh in the form of a bag.

Examples of the material of the filter 31 include: polymers such as polyester, polyurethane and polytetrafluoroethylene; and superelastic metals such as nickel alloys.

The filter 31 may have pores of any size, as long as plaques and the like can be captured while ensuring the blood flow. In preparing the filter 31 by forming pores in a sheet, the diameter of the pores is preferably 30 to 500 μm, and in preparing the filter 31 using a mesh, one side of an aperture of the mesh is preferably 30 to 500 μm. Further, the surface of the filter may be subjected to an antithrombogenic treatment.

The ring 32 may be made of any material as long as it is a flexible wire having elasticity or shape memory property that allows the diameter of the ring 32 to be expanded in the direction vertical to the longitudinal direction, and allows the ring to be folded. However, it is appropriate to use a superelastic metal that can be deformed into various shapes, and can still be restored to the original ring shape. Therefore, the ring is preferably made of a shape memory polymer or a shape memory alloy, and more preferably made of a nickel alloy.

Further, it is desired that the ring 32 have X-ray contrast property to confirm the placement of the filter device in a blood vessel. To impart an X-ray contrast property to the ring, an X-ray contrast material may be incorporated into a portion or the entirety of the ring 32. Examples of the X-ray contrast material that can be used include gold, platinum, tungsten, and palladium alloys.

In the filter device 1 according to the first example, the ring 32 has a cylindrical shape, and is fixed to the opening of the filter 31.

The first wires 41 in the first example are inserted through the first tube 21. One end of the first wires 41 is fixed to the second tube 22, and the other ends of the first wires 41 protrude from the distal end side of the first tube 21 in the longitudinal direction thereof and fixed to the ring 32. The second wires 42 consist of two or more pieces of wires inserted through the first tube 21. One end of the second wires 42 is fixed to the second tube 22, and the other ends of the second wires 42 protrude from the holes 23 of the first tube 21 and fixed to the ring 32.

Examples of suitable materials of the wires include: polymers such as polyester, polyurethane and polytetrafluoroethylene; stainless steel wires; and superelastic metals such as nickel alloys. The first wires and the second wires are required to have such a wire diameter that the opening of the filter portion 3 can be smoothly opened and closed, when the second tube 22 is operated.

Figure 3:
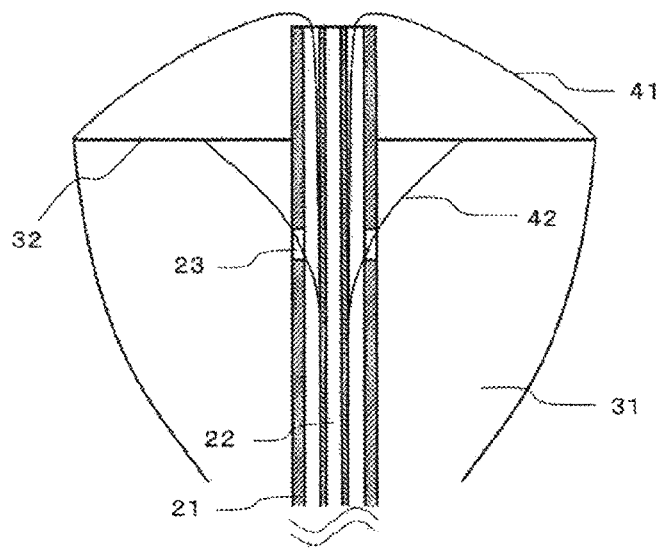
FIG. 3 is an enlarged sectional view of the filter device shown in FIG. 1, when the filter portion is opened.

One end of the first wires 41 and the second wires 42, in the first example, are attached and fixed to the ring 32 as shown in FIG. 3, and the other ends thereof are fixed on the second tube 22.

Figure 4:
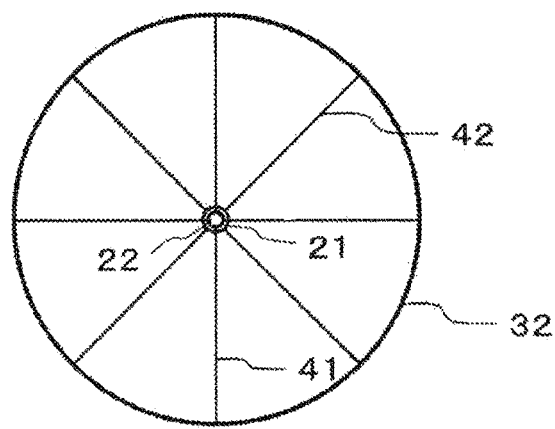
FIG. 4 is an enlarged view of the filter device shown in FIG. 1, seen from the distal end side of the device.

To reliably close the opening of the filter portion 3, the first wires 41 and the second wires 42 are preferably configured such that the fixed positions of the first wires 41 to the ring 32, and the fixed positions of the second wires 42 to the ring 32, are arranged alternately relative to the central axis of the first tube. Further, it is preferred that these fixed positions be arranged such that respective two adjacent fixed positions form equal angles relative to the central axis of the ring 32. As shown in FIG. 4, the filter device 1 includes four pieces of the first wires 41 and four pieces of the second wires 42, and the first wires 41 and the second wires 42 are fixed to the ring 32 alternately, at such intervals that respective two adjacent wires form 45 degrees relative to the central axis.

Figure 5:
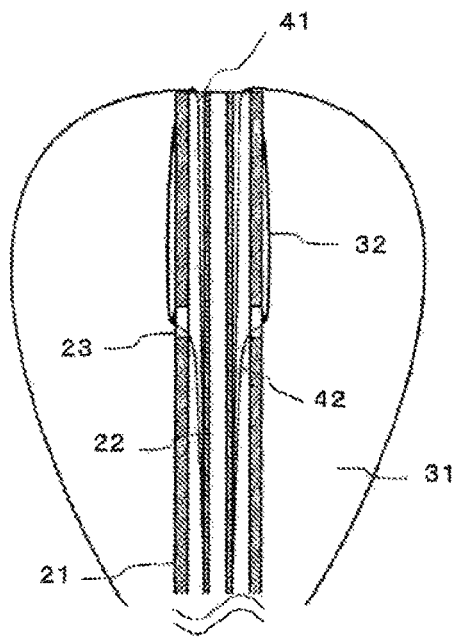
FIG. 5 is an enlarged sectional view of the filter device shown in FIG. 1, when the filter portion is closed.

Further, the filter portion 3 is configured such that the opening of the filter portion 3 can be closed by pulling the second tube 42 towards the proximal end side in the longitudinal direction. When the second tube 22 is pulled towards the proximal end side, in the filter device 1, it is preferred that the fixed portions at which the second wires 42 are in contact with the ring 32 arrive at the holes 23 at the same time as the fixed portions at which the first wires 41 are in contact with the ring 32 arrive at the distal end of the first tube 21. As shown in FIG. 5, the filter device 1 in this Example is configured such that, when the second tube 22 is pulled, the first wires 41 and the second wires 42 fixed on the second tube 22 are pulled, as a result of which the fixed portions at which the first wires 41 are in contact with the ring 32 are brought closer to the distal end of the first tube 21 and, at the same time, the fixed portions at which the second wires 42 are in contact with the ring 32 are brought closer to the holes 23, thereby deforming the cylindrical ring 32. To achieve the deformation of the ring 32 by a single operation, the first wires 41 and the second wires 42 are fixed on the second tube 22.

Figure 6A:
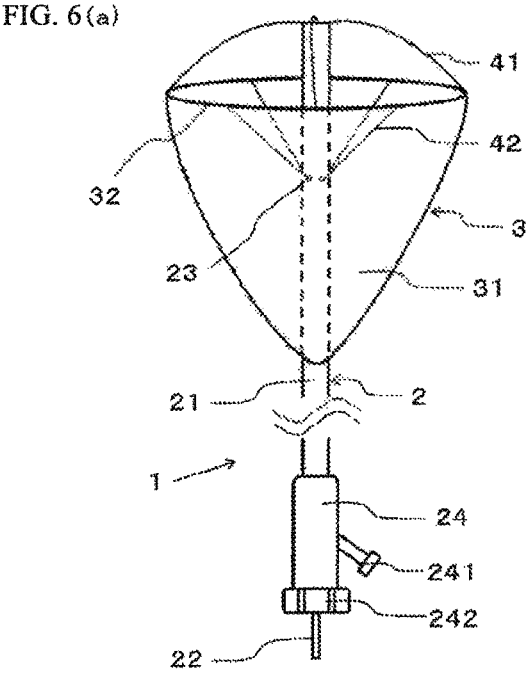
FIGS. 6(a)-(c) are explanatory diagrams showing the process of closing the opening of the filter device shown in FIG. 1.
Figure 6B:
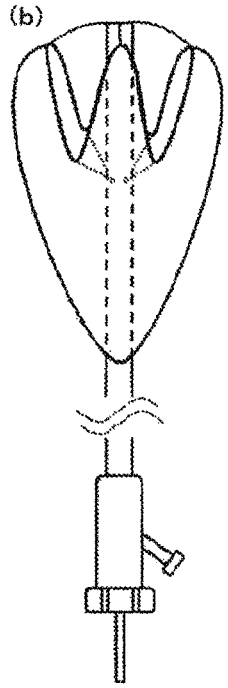
Figure 6C:
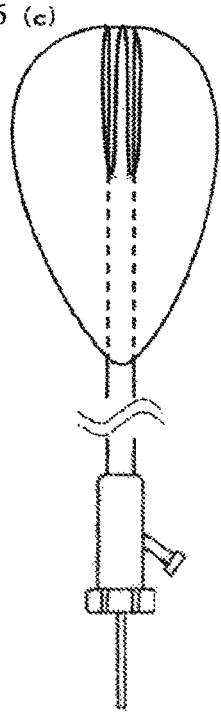

According to the filter device 1 as shown in FIGS. 6(*a*)-(*c*), the fixed portions of the first wires 41 and the second wires 42 to the ring 32 are brought closer to the first tube 21 by holding and pulling the second tube 22 towards the proximal end side and, thus, the cylindrical ring 32 is deformed in the form of waves. As a result, the filter 31 is deformed into a shape having a plurality of mountains and valleys to conform to the shape of the ring 32, and the ring 32 comes into contact with the first tube 21. In this manner, the opening of the filter portion 3 can be closed.

SECOND EXAMPLE

Figure 7:
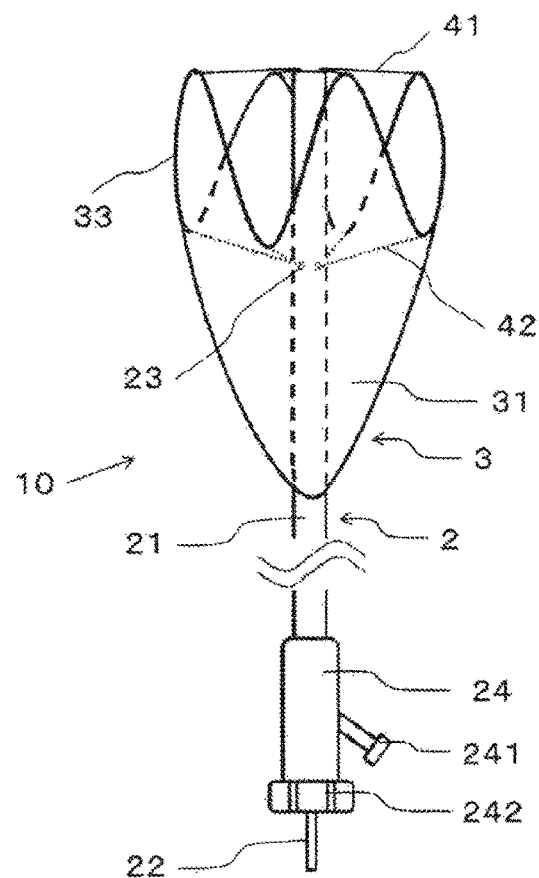
FIG. 7 is an explanatory diagram showing a second example of the filter device.

FIG. 7 is a schematic diagram showing a filter device 10 according to the second example. The filter device 10 in this Example includes: a body portion 2 that allows the filter portion to be moved to a target site in a blood vessel; a filter portion 3 that captures thrombi; and first wires 41 and second wires 42 that open and close the opening of the filter portion 3.

The difference between the filter device 10 of this Example and the filter device 1 described above is that the ring 33 has a shape in which a plurality of mountains facing the distal end side in the longitudinal direction and a plurality of valleys facing the proximal end side in the longitudinal direction are alternately formed. The features other than the above are the same as the filter device 1 described above. The same portions are denoted with the same reference numerals.

The body portion 2 includes: a first tube 21; and a second tube 22 inserted through the lumen of the first tube 21. The second tube 22 is configured such that the proximal end of the second tube 22 protrudes from the proximal end side of the first tube 21, and such that the second tube 22 can be moved relative to the first tube 21. Further, a guide wire can be inserted through the lumen of the second tube 22. By this arrangement, the body portion 2 can be moved along the guide wire placed in a blood vessel in advance, thereby enabling delivery of the filter device 10 to a target affected site.

Figure 2:
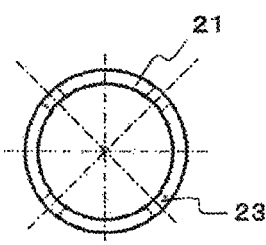
FIGS. 2(a) and (b) are explanatory diagrams showing the first tube included in the filter device shown in FIG. 1.
Figure 2:
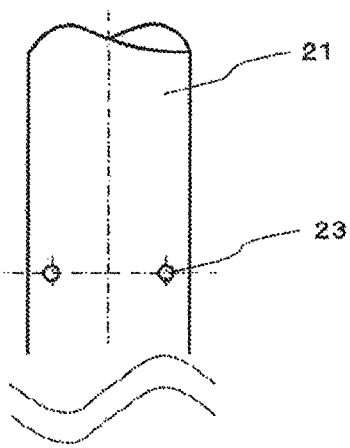

The first tube 21 includes holes 23 through which the second wires 42 to be described later can be inserted. The first tube 21 preferably includes a plurality of the holes 23 in a number corresponding to the number of the second wires 42. Further, when the first tube 21 includes a plurality of the holes 23, the holes 23 are arranged to form substantially equal angles relative to the central axis of the first tube 21, and arranged in the same circumferential direction. As shown in FIGS. 2(*a*) and (*b*), the holes 23 in the second example are formed such that four holes 23 are arranged in the same circumferential direction of the first tube, and the four holes 23 are arranged at such intervals that respective two adjacent holes 23 form 90 degrees relative to the central axis of the first tube 21. Further, a connector 24 is fixed to the proximal end side of the first tube 21 in the longitudinal direction.

To facilitate insertion of a guide wire into the lumen of the second tube 22, it is preferred that the second tube 22 be configured such that the distal end thereof coincides with, or to slightly protrudes from, the distal end of the first tube 21 when the filter portion 3 is opened.

The connector 24 in the second example is fixed to the proximal end side of the first tube 21 as shown in FIG. 7, and includes: a liquid inflow port 241 capable of injecting a physiological saline solution or the like into the lumen of the first tube 21; and a hemostasis valve 242 that prevents the leaking of blood when the second tube 22 is operated and not operated. It is more preferred that the hemostasis valve 242 be configured such that the valve can be opened and closed by a rotary motion or the like. By the above described configuration, the second tube 22 can be operated when the hemostasis valve 242 is opened, and the second tube 22 can be fixed when the hemostasis valve 242 is closed.

The filter portion 3 includes: a filter 31 in the form of a bag; and a ring 33 having a shape in which a plurality of mountains facing the distal end side in the longitudinal direction and a plurality of valleys facing the proximal end side in the longitudinal direction are alternately formed, which is fixed to the opening of the filter 31, and contributes to opening and closing of the opening. As shown in FIG. 7, the filter 31 in the second examples is in the form of a bag, whose opening, when opened, has a shape in which a plurality of mountains facing the distal end side in the longitudinal direction and a plurality of valleys facing the proximal end side in the longitudinal direction are alternately formed. The filter 31 is configured such that the bottom of the bag located at the proximal end side in the longitudinal direction of the first tube, serves as the closed end portion, and the opening of the bag located at the distal end side in the longitudinal direction, serves as the opening. Further, the closed end portion of the filter 31 is fixed to the first tube 21, and the entire shape of the filter device 1 is the shape of an umbrella opened upside down.

In the filter device 10 according to the second example, the ring 33 having a shape in which a plurality of mountains facing the distal end side in the longitudinal direction and a plurality of valleys facing the proximal end side in the longitudinal direction are alternately formed, is fixed to the opening of the filter 31. Specifically, as shown in FIG. 7, the ring 33 in which four mountains and four valleys are formed is fixed to the filter member 31.

The first wires 41 in the second example are inserted through the first tube 21. One end of the first wires 41 is fixed to the second tube 22, and the other ends of the first wires 41 protrude from the distal end side of the first tube 21 in the longitudinal direction thereof and fixed to the ring 33. The second wires 42 consist of two or more pieces of wires inserted through the first tube 21. One end of the second wires 42 is fixed to the second tube 22, and the other ends of the second wires 42 protrude from the holes 23 of the first tube 21 and fixed to the ring 33.

Figure 8:
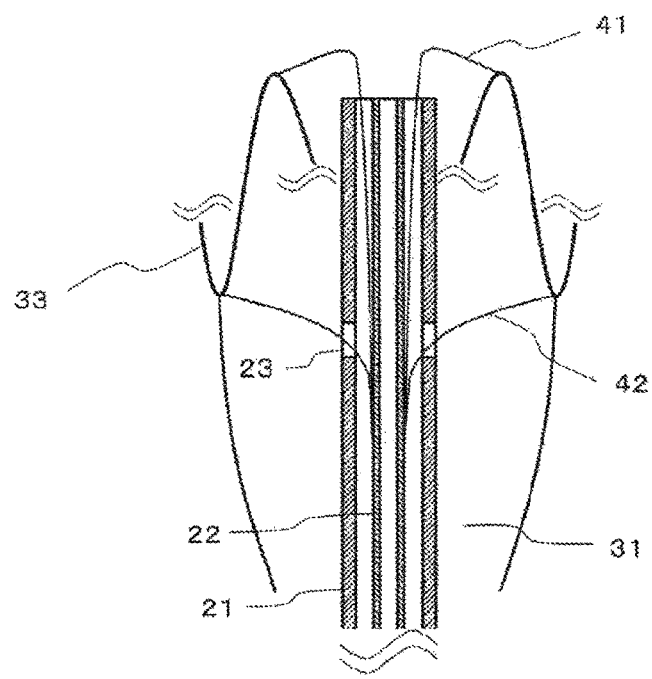
FIG. 8 is an enlarged sectional view of the filter device shown in FIG. 7, when the filter portion is opened.

As shown in FIG. 8, in the filter device 10 according to the second example, one end of the first wires 41 is attached and fixed to the apices of the mountains of the ring 33, and one end of the second wires 42 is fixed to the bottoms of the valleys of the ring 33. Further, the other ends of the first wires 41 and the second wires 42 are fixed on the second tube 22.

Figure 9:
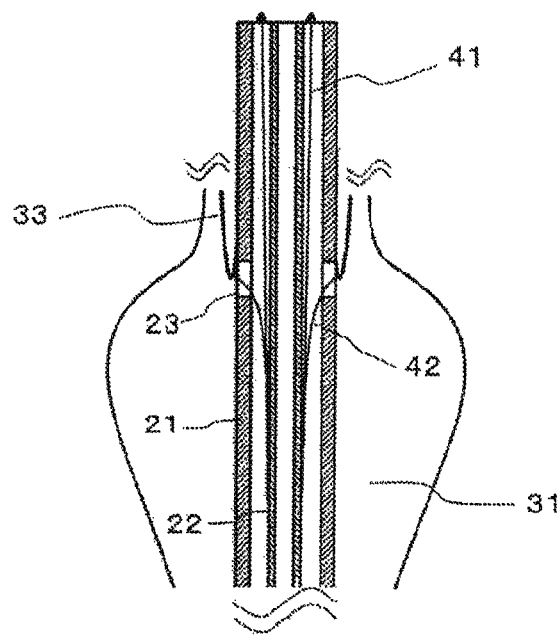
FIG. 9 is an enlarged sectional view of the filter device shown in FIG. 7, when the filter portion is closed.

Further, the filter portion 3 is configured such that the opening of the filter portion 3 can be closed by pulling the second tube 42 towards the proximal end side in the longitudinal direction. When the second tube 22 is pulled towards the proximal end side, in the filter device 10, it is preferred that the fixed portions at which the second wires 42 are in contact with the ring 33 arrive at the holes 23 at the same time as the fixed portions at which the first wires 41 are in contact with the ring 33 arrive at the distal end of the first tube 21. As shown in FIG. 9, the filter device 10 is configured such that, when the second tube 22 is pulled, the first wires 41 and the second wires 42 fixed on the second tube 22 are pulled, as a result of which the apices of the mountains of the ring 33 are brought closer to the distal end of the first tube 21 and, at the same time, the bottoms of the valleys of the ring 33 are brought closer to the holes 23. This allows for deformation of the ring 33 having a shape in which a plurality of mountains facing the distal end side in the longitudinal direction and a plurality of valleys facing the proximal end side in the longitudinal direction are alternately formed. To achieve deformation of the ring 33 by a single operation, the first wires 41 and the second wires 42 are fixed on the second tube 22.

Figure 10:
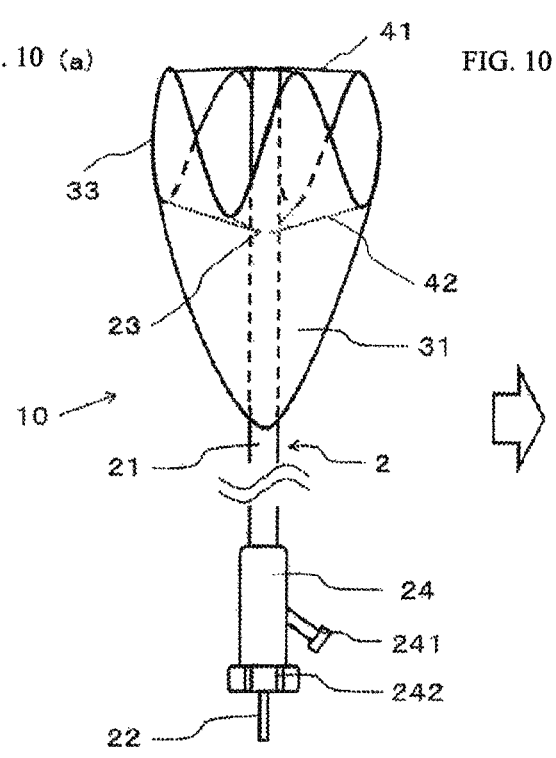
FIGS. 10(a)-(c) are explanatory diagrams showing the process of closing the opening of the filter device shown in FIG. 7.
Figure 10:
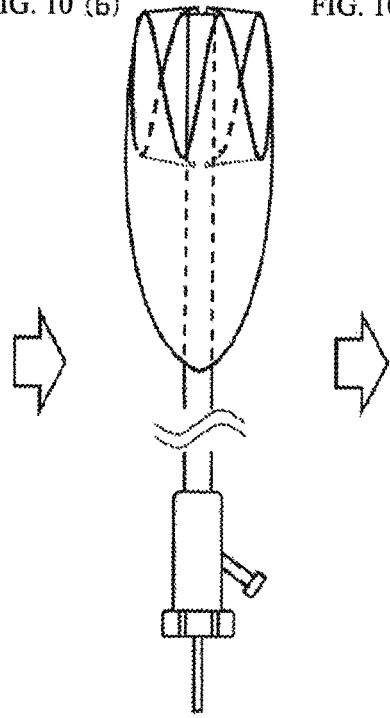
Figure 10:
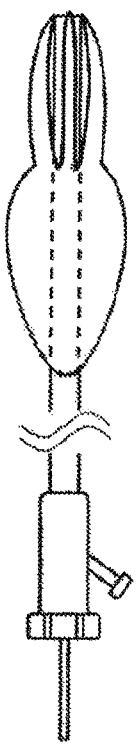

According to the filter device 10 as shown in FIGS. 10(a)-(c), the ring 33 having a shape in which a plurality of mountains facing the distal end side in the longitudinal direction and a plurality of valleys facing the proximal end side in the longitudinal direction are alternately formed, is deformed and brought closer to the first tube 21, by holding and pulling the second tube 22 towards the proximal end side. As a result, the filter 31 is deformed to conform to the shape of the ring 33, and the ring 33 comes into contact with the first tube 21. In this manner, the opening of the filter portion 3 can be closed.

EXAMPLES

Specific Examples of the filter device 10 will now be described, with reference to the drawings.

Example 1

The filter device 10 shown in FIG. 7 was produced. In Example 1, the first tube 21 was formed by connecting a plurality of tubes into a single tube. Specifically, a polyamide tube having an outer diameter of 1.58 mm, an inner diameter of 1.25 mm and a length of about 30 mm was prepared, and four holes 23 each having a diameter of about 0.5 mm were formed at positions about 24 mm from the distal end side of the tube, in the same circumferential direction, and at such intervals that respective two adjacent holes 23 form 90 degrees relative to the central axis of the tube.

A polyimide tube having an inner diameter of 0.6 mm, a thickness of 0.02 mm and a length of 1,200 mm was used as the second tube 22, and inserted through the polyamide tube.

The filter 31 was prepared by using a mesh formed from polyester fibers having a monofilament diameter of 28 μm, and in which one side of an aperture was 100 μm, and by forming the mesh in the form of a bag. The filter 31 was configured such that the opening thereof, when opened, has a shape in which a plurality of mountains facing the distal end side in the longitudinal direction and a plurality of valleys facing the proximal end side in the longitudinal direction were alternately formed.

The ring 33 was prepared using a nickel-titanium alloy wire having a wire diameter of 0.20 mm, and processed such that the ring had a diameter of 32 mm and a length in the longitudinal direction of 20 mm, and that the ring included four mountains and four valleys formed alternately and at regular intervals so that the entire shape of the ring was in the form of waves. Further, the ring 33 was fixed to the filter 31 using polyurethane, and prepared such that the total length of the filter portion 3 was about 55 mm (including the ring 33).

Four pieces of nickel-titanium alloy wires, each having a wire diameter of 42 μm, were used as the first wires 41, and one end of the wires attached to the apices of the mountains of the ring 33.

Further, four pieces of stainless steel wires, each having a wire diameter of 0.15 mm, were used as the second wires 42, and one end of the wires attached to the bottoms of the valleys of the ring 33 by solder.

The other ends of the first wires 41 and the second wires 42 were fixed on the second tube such that, when the second tube 22 was pulled, the bottoms of the valleys of the ring 33 arrived at the holes 23 at the same time as the apices of the mountains of the ring 33 arrived at the distal end of the first tube 21 as shown in FIG. 9. At this time, the first and second wires were fixed on the second tube 22 at positions about 50 mm from the distal end portion of the second tube 22.

Thereafter, a tube which has a three-layer structure composed of an inner layer of polytetrafluoroethylene, an intermediate layer of a stainless steel braid, and an outer layer of polyimide, and which has an outer diameter of 2.0 mm, an inner diameter of 1.6 mm, and a length of about 1,000 mm, was adhered and connected to the proximal end side of the polyamide tube in the longitudinal direction, using an adhesive, and the resultant was used as the first tube 21. Finally, the proximal end side of the filter 31 was fixed to the outer side of the first tube 21 with the adhesive.

Example 2

As the filter device of Example 2, a filter device 11 was produced in the same manner as in Example 1, except that the filter device was configured such that the length of the ring 33 in the longitudinal direction was 15 mm, the total length of the filter portion 3 was about 50 mm, and the holes 23 were formed at positions about 20 mm from the distal end side of the first tube 21.

Example 3

As the filter device of Example 3, a filter device 12 was produced in the same manner as in Example 1, except that the filter device was configured such that the length of the ring 33 in the longitudinal direction was 10 mm, the total length of the filter portion 3 was about 45 mm, and the holes 23 were formed at positions about 16 mm from the distal end side of the first tube 21.

Comparative Example 1

Figure 11:
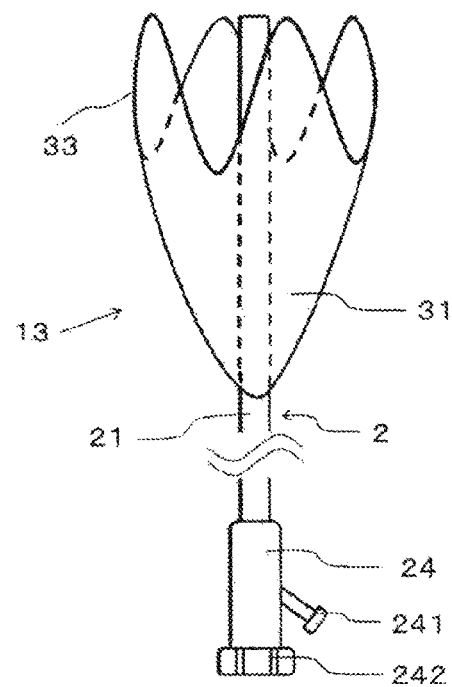
FIG. 11 is an explanatory diagram showing the filter device of Comparative Example 1.

As the filter device of Comparative Example 1, a filter device 13 was produced in the same manner as in Example 1, except that the second tube 22, the holes 23, the first wires 41 and the second wires 42 were not provided as shown in FIG. 11. In this Comparative Example, the filter device does not have a mechanism to close the filter portion since the first wires 41 and the second wires 42 are absent.

Comparative Example 2

Figure 12:
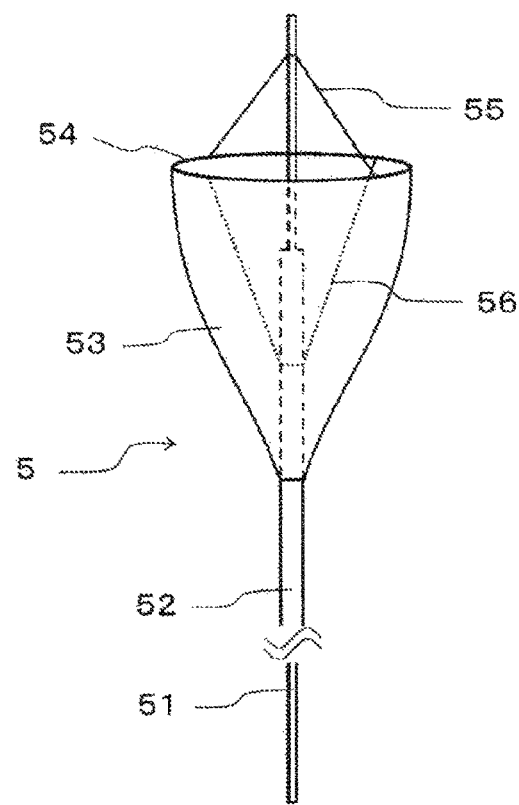
FIG. 12 is an explanatory diagram showing the intravascular blood filter of Comparative Example 2.

As the filter device of Comparative Example 2, an intravascular blood filter 5 disclosed in JP 4067353 B2 was prepared. Specifically, as shown in FIG. 12, the intravascular blood filter 5 includes: a core material 51; a catheter member 52 provided to be slidable on the core material 51; a filter 53 whose distal end side forms an opening, and whose proximal end side is fixed to the distal end side of the catheter member 52; a filter ring 54 provided at the opening of the filter member 53 and facilitates the folding and expansion of the filter member 53; two pieces of wires 55 for pulling forward that connect the filter ring 54 with the distal end side of the core material 51; and two pieces of wires 56 for pulling backward that connect the member 53 for opening and closing the filter, with the catheter member 52, in the interior of the filter member 53. In the intravascular blood filter 5, it is possible to deform the filter and close the opening thereof by moving the core material 51 relative to the catheter member 52.

A stainless steel wire having an outer diameter of 0.55 mm and a length of 1,200 mm was used as the core material 51.

A polyimide tube having an outer diameter of 1.7 mm, an inner diameter of 1.6 mm and a length of about 1,000 mm was used as the catheter member 52, and the core material 51 was inserted into the lumen of the catheter member 52.

The filter 53 was prepared using a mesh formed from polyester fibers having a monofilament diameter of 28 µm, and in which one side of an aperture was 100 µm. The proximal end side of the filter 53 was fixed to the distal end side of the catheter member 52 so that the distal end side of the filter 53 forms an opening.

The filter ring 54 was prepared using a nickel-titanium alloy wire having a wire diameter of 0.10 mm and processed in the form of a ring having a diameter of 32 mm. Further, the filter ring 54 was fixed to the filter 53 using polyurethane, and prepared such that the total length of the filter portion 53 was about 55 mm.

Two pieces of nickel-titanium alloy wires having a wire diameter of 42 µm were used as the wires 55 for pulling forward, and one end of the wires 55 fixed to the filter ring 54, and the other ends of the wires 55 were fixed to the core material 51 at positions 10 mm from the distal end thereof.

Further, two pieces of nickel-titanium alloy wires having a wire diameter of 42 µm were used as the wires 56 for pulling backward, and one end of the wires 56 fixed to the filter ring 54, and the other ends of the wires 56 were fixed to the catheter member 52 at positions 40 mm from the distal end thereof.

The wires 55 for pulling forward and the wires 56 for pulling backward were fixed to the filter ring 54 such that the fixed positions of the wires 55 and the wires 56 are arranged alternately at such intervals that respective two adjacent fixed positions form 90 degrees relative to the central axis of the catheter member 52.

Figure 13:
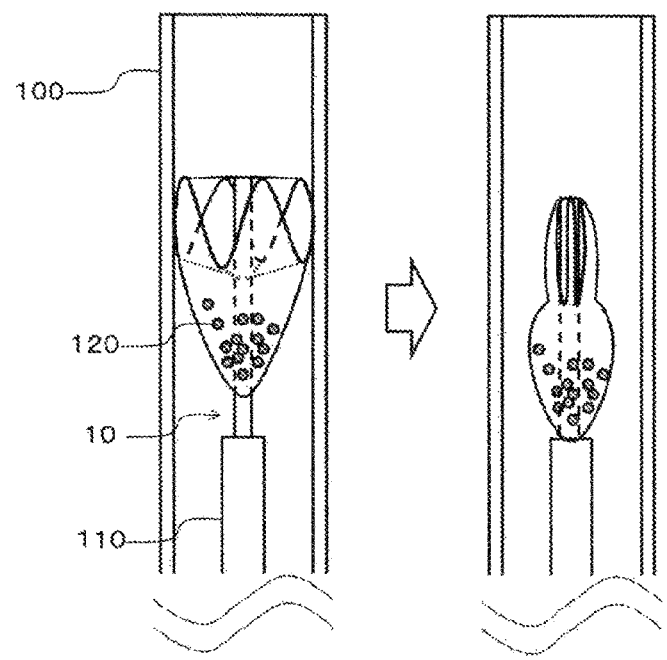
FIG. 13 is an explanatory diagram showing an experimental system for carrying out a missing rate experiment using simulated embolic particles.

Comparative Experiment to Determine Missing Rate Using Simulated Embolic Particles As shown in the schematic diagram of an experiment model for the comparison of missing rate shown in FIG. 13, a tube 100 having an inner diameter of 30 mm was prepared and the tube was filled with water. Simulated embolic particles 120 having a particle size of 150 µm were introduced into the mesh portion, and the filter device was set in the tube 100. Thereafter, the filter device was allowed to pass through a sheath introducer 110 having a diameter of a 10 Fr., and then the operation of removing the filter device 10 was carried out. The comparative experiment of the missing rate was carried out by counting the number of the simulated embolic particles collected, and the number of the simulated embolic particles flowed out of the filter device. The term "missing rate" as used herein refers to the ratio of the number of the simulated embolic particles failed to be collected and flowed out of the filter device relative to the number of the simulated embolic particles introduced into the device, shown as a percentage. When carrying out the experiment for each of the filtering devices of Examples 1 to 3, the second tube 22 was held and pulled towards the proximal end side to close the opening of the filter portion 3, and carry out the removal operation. As a result, each of the filtering devices of Examples 1 to 3, in which the opening of the filter portion 3 can be closed, exhibited a missing rate of less than 5%, whereas the filtering device of Comparative Example 1 exhibited a missing rate of about 42%, as shown in Table 1. The above results have revealed that it is desirable to securely close the opening of the filter portion so that the captured emboli can be prevented from being released into the body again.

TABLE 1

|  | Presence or absence of mechanism for opening and closing filter | Length of ring in longitudinal direction (mm) | Total length of filter portion (mm) | Number of particles introduced (number) | Number of collected particles (number) | Number of missed particles (number) | Missing rate (%) |
| --- | --- | --- | --- | --- | --- | --- | --- |
| Example 1 | Yes | 20 | 55 | 595 | 588 | 7 | 1.2 |
| Example 2 | Yes | 15 | 50 | 593 | 575 | 18 | 3.0 |
| Example 3 | Yes | 10 | 45 | 539 | 520 | 19 | 31.5 |
| Comparative Example 1 | No | 20 | 55 | 581 | 340 | 241 | 41.5 |

Experiment on Torsional Twist Upon Rotation

In the intravascular blood filter 5 described in Comparative Example 2, the opening of the filter member 53 was closed by holding the core material 51 and allowing the core material 51 to move forward towards the distal end side relative to the catheter member 52. Subsequently, the core material 51 was held and rotated in a state where the catheter member 52 was fixed. Further, the core material 51 was pulled relative to the catheter member 52, to close the filter portion. As a result, the wires 55 and 56 for pulling were entangled with the core material 51 or the catheter member 52, failing to sufficiently close the filter member 53.

In the intravascular blood filter 5 of the Comparative Example 2, the core material functions as a guide wire, and we confirmed that, when the function of the core material as a guide wire for guiding the filter to a target site is used during the procedure, the core material as the guide wire is rotated, causing the wires for pulling to be entangled with the core material or the catheter member. In this Comparative Example, the opening of the filter portion may not be sufficiently controlled, possibly resulting in a failure to capture the emboli generated during the procedure. In contrast, in the filter device 10 described in Example 1, a guide wire can be inserted through the lumen of the second tube, and the device can be delivered along the guide wire placed in a blood vessel in advance and, thus, there is no need to rotate the device, in the first place.

INDUSTRIAL APPLICABILITY

Our filter device is capable, by being placed in the ascending aorta during an endovascular treatment such as a catheter ablation procedure to treat atrial fibrillation or a transcutaneous aortic valve replacement procedure, capturing and collecting emboli generated by the treatment, and thus preventing the occurrence of infarction.

The invention claimed is:

1. A filter device comprising:

a first tube having holes on a side surface thereof;

a second tube inserted through said first tube and protruding from a proximal end side of said first tube in a longitudinal direction thereof;

a filter arranged such that said filter has a closed end portion on the proximal end side in the longitudinal direction of said first tube, and such that a distal end side of said filter in said longitudinal direction forms an opening;

a ring fixed to said opening and having elasticity or a shape memory property;

first wires inserted between said first tube and said second tube, wherein proximal ends of said first wires are fixed to said second tube, and distal ends of said first wires protrude from the distal end side of said first tube in the longitudinal direction thereof and are fixed to portions of said ring; and second wires inserted between said first tube and said second tube, wherein the proximal ends of said second wires are fixed to said second tube, and the distal ends of said second wires protrude from said holes and are fixed to portions of said ring;

wherein said opening can be opened and closed in the form of a bag when the proximal end side of said filter in the longitudinal direction is defined as a bottom, and said opening can be closed by pulling said second tube towards the proximal end side in the longitudinal direction.

2. The filter device according to claim 1, wherein said holes are arranged to form equal angles relative to a central axis of said first tube, and arranged on a same circumference.

3. The filter device according to claim 1, wherein said ring has a cylindrical shape, and fixed positions of said first wires to said ring, and the fixed positions of said second wires to said ring are arranged alternately relative to a central axis of said first tube.

4. The filter device according to claim 1, wherein said ring includes a plurality of mountains facing the distal end side in said longitudinal direction, and a plurality of valleys facing the proximal end side in said longitudinal direction, which mountains and valleys are alternately formed, fixed positions of said first wires to said ring are provided at apices of said mountains, and fixed positions of said second wires to said ring are provided at bottoms of said valleys.

* * * * *